United States Patent
Chen et al.

(10) Patent No.: US 7,071,325 B2
(45) Date of Patent: Jul. 4, 2006

(54) DNA MOLECULE FOR DETECTING GLYPHOSATE TOLERANT WHEAT PLANT 33391 AND PROGENY THEREOF

(75) Inventors: Guilan Chen, Chesterfield, MO (US); Catherine M. Hironaka, Dublin, CA (US); Hua-ping Zhou, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 162 days.

(21) Appl. No.: 10/737,487

(22) Filed: Dec. 16, 2003

(65) Prior Publication Data

US 2004/0133940 A1 Jul. 8, 2004

Related U.S. Application Data

(62) Division of application No. 09/682,597, filed on Sep. 25, 2001, now Pat. No. 6,689,880.

(60) Provisional application No. 60/236,762, filed on Sep. 29, 2000, provisional application No. 60/236,653, filed on Sep. 29, 2000.

(51) Int. Cl.
*C12N 21/04* (2006.01)
(52) U.S. Cl. .................................................. 536/24.3
(58) Field of Classification Search ................ 536/24.3
See application file for complete search history.

(56) References Cited

U.S. PATENT DOCUMENTS

| | | | |
|---|---|---|---|
| 5,633,435 A | 5/1997 | Barry et al. | 800/288 |
| 5,948,956 A | 9/1999 | Lee et al. | 800/320 |

FOREIGN PATENT DOCUMENTS

| | | |
|---|---|---|
| EP | 1 167 531 A1 | 1/2002 |
| WO | WO 99/46396 | 9/1999 |

OTHER PUBLICATIONS

McElroy et al 1990, The Plant Cell 2:163-171.*
Saroha et al., Glyphosate tolerant crops: tenes and enzymes, *J. Plant Biochem and Biotech*, 7:65-72 (1998).
Windels et al., Development of a line specific GMO detection method a case study, *Med,. Fac. Landbouww. Univ. Gent.* 64/5b: 459-62 (1999).
Zhou et al., Glyphosate tolerant CP4 and GOX genes as a selectable marker in wheat transformation, *Plant Cell Reports* 15:159-63 (1995).

* cited by examiner

*Primary Examiner*—David H Kruse
(74) *Attorney, Agent, or Firm*—M. Todd Rands

(57) ABSTRACT

The present invention provides a DNA construct composition that relates to transgenic glyphosate tolerant wheat plants. The invention relates to the wheat plant 33391, the progeny thereof and to methods for the detection of wheat plant 33391 and its progeny and compositions thereof using an insertion junction sequence designated SEQ ID NO: 6.

2 Claims, 3 Drawing Sheets

DNA MOLECULE FOR DETECTING GLYPHOSATE TOLERANT WHEAT PLANT 33391 AND PROGENY THEREOF

This application is a divisional application of non-provisional U.S. application Ser. No. 09/682,597 filed Sep. 25, 2001 now U.S. Pat. No. 6,689,880, which claims the benefit of priority to U.S. Provisional Application Ser. No. 60/236,762 filed Sep. 29, 2000 and U.S. Provisional Application Ser. No. 60/236,653 filed Sep. 29, 2000.

FIELD OF THE INVENTION

The present invention relates to the field of plant molecular biology, more specifically the invention relates to a DNA construct for conferring improved glyphosate tolerance to a wheat plant. The invention more specifically relates to a glyphosate tolerant wheat plant 33391 and progeny thereof and to assays for detecting the presence of wheat plant 33391 DNA in a sample and compositions thereof.

BACKGROUND OF THE INVENTION

Wheat is an important crop and is a primary food source in many areas of the world. The methods of biotechnology have been applied to wheat for improvement of the agronomic traits and the quality of the product. One such agronomic trait is herbicide tolerance, in particular, tolerance to glyphosate herbicide. This trait in wheat is conferred by the expression of a transgene in the wheat plants (Zhou et al., Plant Cell Rep. 15:159–163, 1995). The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421–477, 1988). For this reason, it is often necessary to screen a large number of events in order to identify an event characterized by optimal expression of a introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Windels et al. (Med. Fac. Landbouww, Univ. Gent 64/5b:459–462, 1999), who identified glyphosate tolerant soybean event 40-3-2 by PCR using a primer set spanning the junction between the insert and flanking DNA, specifically one primer that included sequence from the insert and a second primer that included sequence from flanking DNA.

This invention relates to the improved glyphosate herbicide tolerant wheat (*Triticum aestivum*) plant 33391 and to a DNA plant expression construct of wheat plant 33391 and the detection of the transgene/genomic insertion region in wheat 33391 and progeny thereof.

SUMMARY OF THE INVENTION

According to one aspect of the invention, a DNA construct is provided that when expressed in wheat plant cells and wheat plants confers improved tolerance to glyphosate herbicide. This invention relates to the methods for producing and selecting a glyphosate tolerant wheat plant containing the DNA construct pMON30139. The DNA construct, pMON30139 consists of two transgene expression cassettes. The first expression cassette consists of a rice (*Oryzae sativa*) actin 1 promoter (P-Os.Act1) and intron (I-Os.Act1) operably joined to an *Arabidopsis* EPSPS chloroplast transit peptide sequence (TS-At.EPSPS), operably connected to a gene (AGRTU.aroA:CP4) encoding a glyphosate resistant 5-enol-pyruvylshikimate-3-phosphate synthase (EPSPS) isolated from *Agrobacterium tumefaciens* (AGRTU) sp. strain CP4, operably connected to a nopaline synthase transcriptional terminator (T-AGRTU.nos). The second transgene expression cassette consists of the cauliflower mosaic virus (CaMV) 35S promoter (P-CaMV.35S:en) containing a tandem duplication of the enhancer region, operably connected to a *Zea mays* Hsp70 intron (I-Zm.Hsp70), operably connected to a nucleic acid sequence encoding an *Arabidopsis thaliana* EPSPS chloroplast transit peptide sequence, operably connected to a gene encoding a glyphosate resistant 5-enol-pyruvylshikimate-3-phosphate synthase isolated from *Agrobacterium tumefaciens* sp. strain CP4, operably connected to a nopaline synthase transcriptional terminator. These expression cassettes are in tandem and flanked by DNA regions that contain *Agrobacterium tumefaciens* DNA sequences (RB and LB) as a components of the process that is used in an Agrobacterium mediated method to insert of the expression cassettes into a wheat genome.

According to another aspect of the invention, wheat 33391 seed comprising such DNA molecules are provided as deposited with the ATCC, accession #PTA-2347. This aspect of the invention thus relates to the seeds of wheat 33391, to the plants of wheat 33391, to the plant parts of wheat 33391 that includes pollen and ovules, and to the methods for producing an improved glyphosate tolerant wheat plant by crossing the wheat plant 33391 with itself or another wheat plant.

According to another aspect of the invention, compositions and methods are provided for detecting the presence of the transgene/genomic insertion region from wheat 33391 plants and seeds. According to one aspect of the invention, DNA molecules are provided that comprise at least one transgene/genomic insertion region sequence of wheat 33391 selected from the group consisting of SEQ ID NO:5 and SEQ ID NO:6 and complements thereof, wherein an insertion region sequence spans the junction between heterologous DNA inserted into the wheat genome and DNA from the wheat genome flanking the insertion site and is diagnostic for the event. Included are DNA sequences that comprise a sufficient length of polynucleotides of transgene insert sequence and a sufficient length of polynucleotides of wheat genomic sequence from wheat 33391 of SEQ ID NO:5 that are useful as primer sequences for the production of an amplicon product diagnostic for wheat 33391. Included are DNA sequences that comprise a sufficient length of polynucleotides of transgene insert sequence and a sufficient length of polynucleotides of wheat genomic sequence from wheat 33391 of SEQ ID NO:6 that are useful as primer sequences for the production of an amplicon product diagnostic for wheat 33391.

According to another aspect of the invention DNA molecules are provided that are diagnostic for wheat 33391. This aspect of the invention is directed to the wheat 33391 containing at least one novel DNA molecule. DNA molecules comprising nucleic acid primers are provided that provide at least one novel DNA amplicon product of wheat 33391 consisting of SEQ ID NO:7 and SEQ ID NO:8, or the complements thereof. Such DNA amplicons are diagnostic for wheat 33391. Nucleic acid amplification of genomic DNA of the wheat 33391 produces an amplicon comprising such diagnostic DNA sequences. The invention provides isolated DNA molecules that comprise a sufficient length of transgene insert sequence and a sufficient length of wheat genomic sequence from wheat 33391 to function as primer sequences for the production of an amplicon product diagnostic for wheat 33391.

According to another aspect of the invention, methods of detecting the presence of DNA corresponding to the wheat 33391 in a sample are provided. Such methods comprise: (a) contacting the sample comprising DNA with a primer set that, when used in a nucleic-acid amplification reaction with genomic DNA from wheat 33391, produces an amplicon that is diagnostic for wheat 33391; (b) performing a nucleic acid amplification reaction, thereby producing the amplicon; and (c) detecting the amplicon.

According to another aspect of the invention, a kit is provided for the detection of wheat 33391. The kit includes at least one DNA sequence of sufficient length of polynucleotides complementary to SEQ ID NO:5 or SEQ ID NO:6, wherein the DNA sequences are useful as primers or probes that hybridize to isolated DNA from wheat 33391 or its progeny.

According to another aspect of the invention, methods of producing a wheat plant with improved tolerance to glyphosate are provided that comprise the steps of: (a) sexually crossing a first parental wheat line comprising the pMON30139 construct that confers improved tolerance to application of glyphosate, and a second parental wheat line that lacks glyphosate tolerance, thereby producing a plurality of progeny plants; and (b) selecting a progeny plant that tolerates application of glyphosate. Such methods are useful for introgressing the glyphosate tolerant trait into different genetic backgrounds. Such methods may optionally comprise the further step of back-crossing the progeny plant to the second parental wheat line to produce a wheat plant that tolerates application of glyphosate.

The foregoing and other aspects of the invention will become more apparent from the following detailed description and accompanying drawings.

DETAILED DESCRIPTION OF THE EMBODIMENTS

Figure 1:
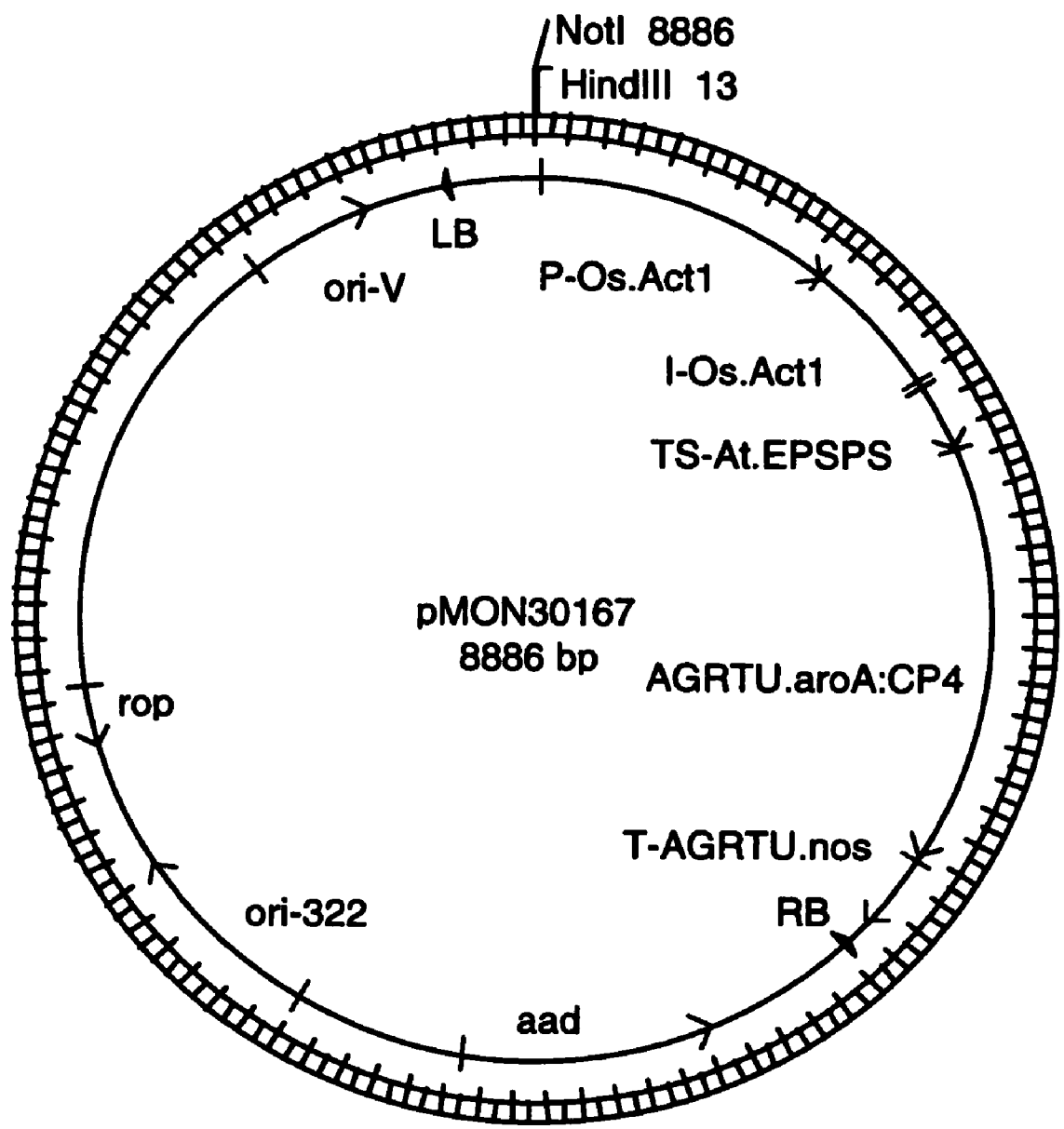
FIG. 1. Plasmid map of pMON30167
FIG. 2. Plasmid map of pMON42411
FIG. 3. Plasmid map of pMON30139

This application claims the benefit of U.S. Provisional Application No. 60/236,653, filed Sep. 29, 2000 and U.S. Provisional Application No. 60/236,762 filed Sep. 29, 2000. The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR § 1.822 is used.

As used herein, the term "wheat" means *Triticum aestivum* (including spring, winter, and facultative wheat varieties) any other wheat species that can be bred with *Triticum aestivum*, including but not limited to durum wheat (*Triticum durum*), spelt (*Triticum spelta*), and emmer (*Triticum dicoccum*). Also encompassed are plants that are produced by conventional techniques using *Triticum aestivum* as a parent in a sexual cross with a non-*Triticum* species (such as rye [*Secale cereale*]), including but not limited to triticale.

As used herein, the term "comprising" means "including but not limited to".

"Glyphosate" refers to N-phosphonomethylglycine and its salts. Glyphosate is the active ingredient of Roundup® herbicide (Monsanto Co, St. Louis, Mo.). Treatments with "glyphosate herbicide" refer to treatments with the Roundup®, Roundup Ultra® herbicide or any other formulation containing glyphosate. For the purposes of the present invention, the term "glyphosate" includes any herbicidally active form of N-phosphonomethylglycine (including any salt thereof) and other forms that result in the production of the glyphosate anion in plants. Treatments with "glyphosate" refer to treatments with the Roundup® or Roundup Ultra® herbicide formulation, unless otherwise stated. Plant transformation and regeneration in tissue culture use glyphosate or salts of glyphosate. Whole plant assays use formulated Roundup® or Roundup Ultra®. Additional formulations with herbicide activity that contain N-phosphonomethylglycine or any of its salts are herein included as a glyphosate herbicide.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. The "event" of the present invention comprises wheat 33391 seed having ATCC accession No. PTA-2347 and wheat plants grown from the wheat 33391 and progeny thereof. A wheat plant that tolerates a sufficient amount of glyphosate herbicide to control the weeds in a field without affecting the wheat plant can be bred by first sexually crossing a first parental wheat plant consisting of a wheat plant containing the expression cassettes of pMON30139 that confers improved tolerance to application of glyphosate herbicide, and a second parental wheat plant that lacks the tolerance to glyphosate herbicide, thereby producing a plurality of first progeny plants; and then selecting a first progeny plant that is tolerant to application of glyphosate herbicide; and selfing the first progeny plant, thereby producing a plurality of second progeny plants; and then selecting from the second progeny plants a glyphosate herbicide tolerant plant. These steps can further include the back-crossing of the first glyphosate tolerant progeny plant or the second glyphosate tolerant progeny plant to the second parental wheat plant or a third parental wheat plant, thereby producing a wheat plant that tolerates the application of glyphosate herbicide. A wheat crop comprising wheat 33391 seeds or progeny thereof can be planted in a field and treated with a sufficient amount of glyphosate herbicide to control the weeds without significantly affecting the wheat crop. A sufficient amount of glyphosate herbicide is about 8 ounces/acre or more, 16 ounces/acre or more, 32 ounces/acre or more, or 64 ounces/acre or more. Any glyphosate containing herbicide formulation can be used to control weeds in a wheat crop comprising wheat 33391 plants or progeny thereof.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987) herein incorporated by reference in its entirety; Poehlman, J. M. (1987); Breeding Field Crops, 3rd ed. Van Nostrand Reinhold, N.Y., Knott, D. R. (1987); herein incorporated by reference in its entirety The Application of Breeding Procedures to Wheat, p. 419–427. In E. G. Heyne (ed.) In "Wheat and Wheat Improvement", Madison, Wis. herein incorporated by reference in its entirety. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The DNA molecules of the present invention can by used as molecular markers in a marker assisted breeding (MAB) method. DNA molecules of the present invention can be used in methods, such as, AFLP markers, RFLP markers, RAPD markers, SNPs, and SSRs that identify genetically linked agronomically useful traits as described by Walton, *Seed World* 22–29 (July, 1993), the entirety of which is herein incorporated by reference; Burow and Blake, *Molecular Dissection of Complex Traits,* 13–29, Eds. Paterson, CRC Press, New York (1988), the entirety of which is herein incorporated by reference). The improved glyphosate tolerance trait of wheat plant 33391 can be tracked in the progeny of a cross with wheat plant 33391 and any other wheat cultivar or variety using the MAB methods. The DNA molecules are markers for this trait and in MAB methods that are well known in the art can be used to track glyphosate tolerance in wheat where wheat plant 33391 was a parent or ancestor.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from wheat event 33391 (whether from a wheat plant or from a sample that includes DNA from the event). Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs or sets can be used for amplification of a nucleic acid sequence, e.g., by the polymerase chain reaction (PCR) or other conventional nucleic-acid amplification methods.

Probes and primers are generally 8 polynucleotides or more in length, 18 polynucleotides or more, 24 polynucleotides or more, 30 polynucleotides or more. Polynucleotides useful as probes and primers that are of sufficient length to hybridize specifically to a target sequence under stringent conditions for hybridization. Probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual,* 2nd ed., vol. 1–3, ed. Sambrook et al., Cold Spring Harbor Laboratory Press, Cold Spring Harbor, N.Y., 1989 (hereinafter, "Sambrook et al., 1989") herein incorporated by reference in its entirety; *Current Protocols in Molecular Biology,* ed. Ausubel et al., Greene Publishing and Wiley-Interscience, New York, 1992 (with periodic updates) (hereinafter, "Ausubel et al., 1992") herein incorporated by reference in its entirety; and Innis et al., *PCR Protocols: A Guide to Methods and Applications*, Academic Press: San Diego, 1990 herein incorporated by reference in its entirety.

PCR-primer pairs can be derived from a known sequence, for example, by using computer programs intended for that purpose such as Primer (Version 0.5, © 1991, Whitehead Institute for Biomedical Research, Cambridge, Mass.) herein incorporated by reference in its entirety.

Primers and probes based on the flanking DNA and insert sequences disclosed herein can be used to confirm (and, if necessary, to correct) the disclosed sequences by conventional methods, e.g., by re-cloning and sequencing such sequences.

The nucleic-acid probes and primers of the present invention hybridize under stringent conditions to a target DNA sequence. Any conventional nucleic acid hybridization or amplification method can be used to identify the presence of DNA from a transgenic event in a sample.

The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58 herein incorporated by reference in its entirety; Kanehisa, (Nucl. Acids Res. 12:203–213, 1984, herein incorporated by reference in its entirety); and Wetmur and Davidson, (J. Mol. Biol. 31:349–370, 1988, herein incorporated by reference in its entirety). Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. A stringent conditions, for example, is to wash the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

Regarding the amplification of a target nucleic-acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether the wheat plant resulting from a sexual cross contains an transgenic event, genomic DNA from a wheat plant may be subjected to nucleic acid amplification using a primer pair that includes a primer derived from flanking sequence in the genome of the plant adjacent to the insertion site of inserted heterologous DNA and a second primer derived from the inserted heterologous DNA to produce an amplicon that is diagnostic for the presence of the event. The amplicon is of a length and has a sequence that is diagnostic for the event. Alternatively, a primer pair can be derived from flanking sequence on both sides of the inserted DNA so as to produce an amplicon that includes the entire insert.

Nucleic acid amplification can be accomplished by any of the various nucleic acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. Any well known method for nucleic acid amplification may be used in the practice of the present invention. The sequence of the heterologous DNA insert or flanking sequence from wheat 33391 event, ATCC accession No. PTA-2347 can be verified (and corrected if necessary) by amplifying such sequences from the event using primers derived from the sequences provided herein followed by standard methods of DNA sequencing of the PCR amplicon or of the cloned DNA molecule.

The amplicon produced by these methods may be detected by a plurality of techniques. Agarose gel electrophoresis and staining with ethidium bromide is a common well known method of detecting DNA amplicons. Another method is Genetic Bit Analysis (Nikiforov, et al. Nucleic Acid Res. 22:4167–4175, 1994) where an DNA oligonucleotide is designed which overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

An additional method is the Pyrosequencing technique as described by Winge (Innov. Pharma. Tech. 00:18–24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal which is measured. A light signal indicates the presence of the transgene/flanking sequence due to successful amplification, hybridization, and single or multi-base extension.

Fluorescence Polarization as described by Chen, et al., (Genome Res. 9:492–498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the prescence of the transgene/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene sequence due to successful amplification and hybridization.

Molecular Beacons have been described for use in sequence detection as in Tyangi, et al. (Nature Biotech. 14:303–308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene sequence due to successful amplification and hybridization.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Figure 2:
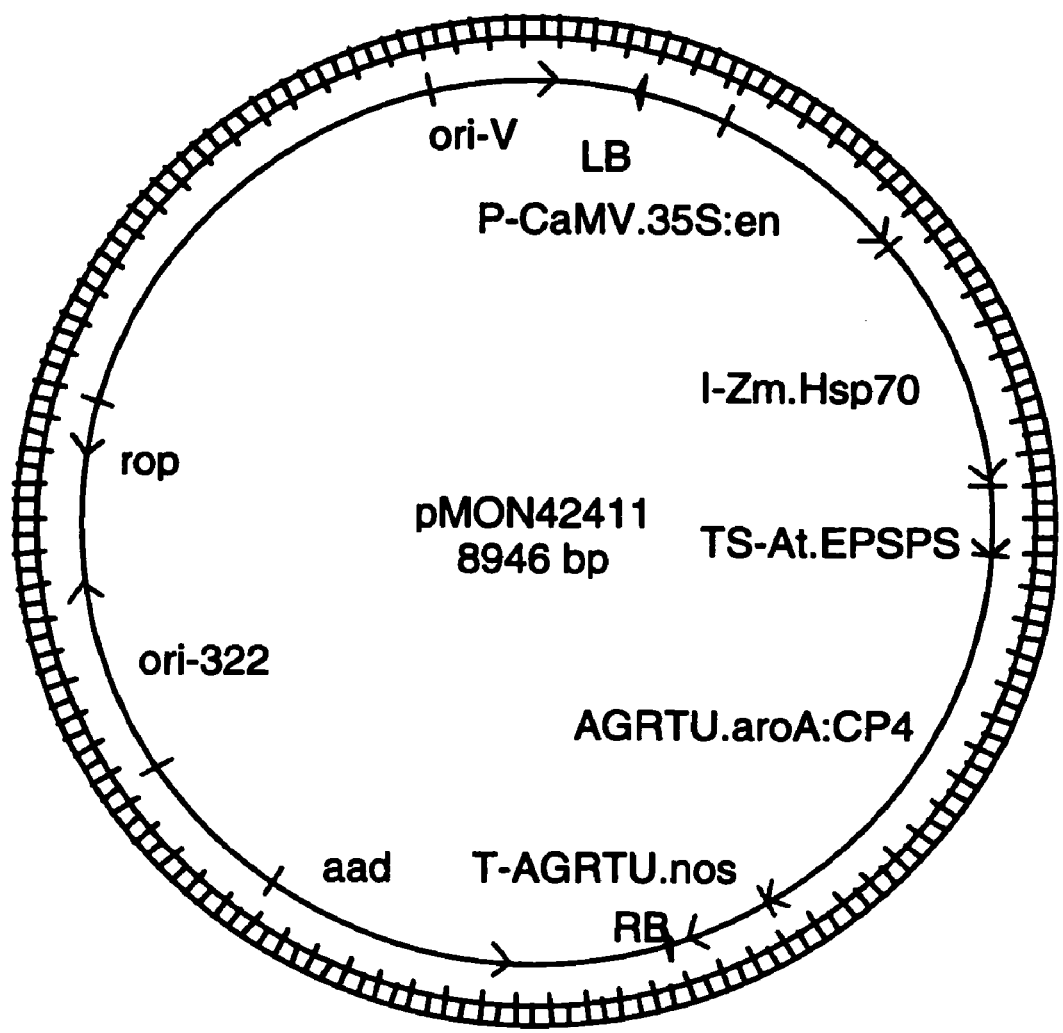
Figure 3:
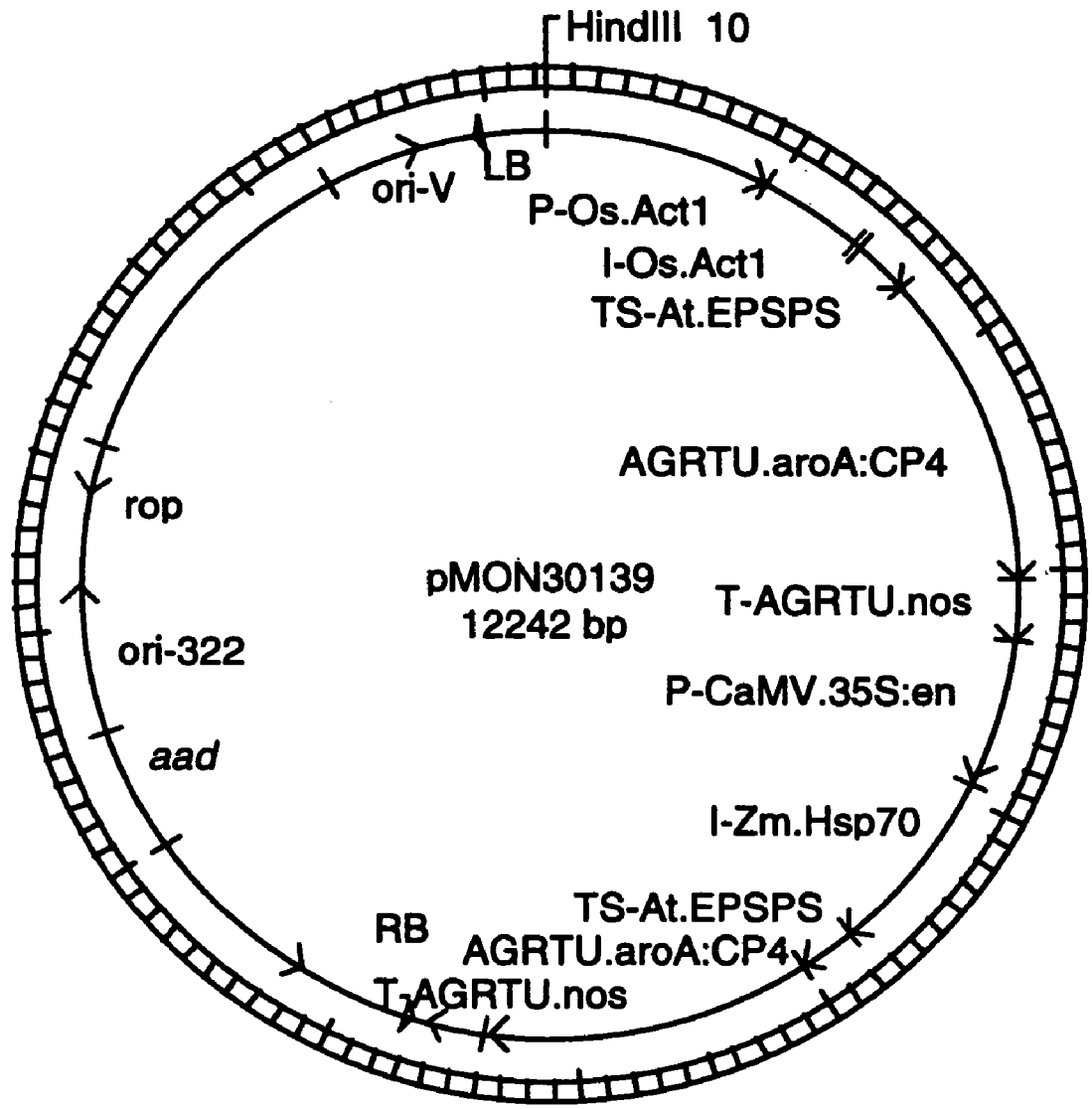

The transgenic wheat plants are generated by *Agrobacterium*-mediated transformation of wheat embryos by the method of Cheng et al. (Plant Physiol. 115:971–980, 1997) using the binary vectors of the present invention and a modification of the glyphosate selection conditions of Zhou et al. (Plant Cell Rep. 15:159–163, 1995). Other methods of wheat transformation are known to those skilled in the art of wheat transformation, such as, gene gun or particle bombardment and can be used to insert the expression cassettes of the present invention into the genome of wheat cells. The T-DNA of pMON30139 (FIG. 3) contains two expression cassettes that collectively confer a high level of tolerance to glyphosate herbicide. The first transgene expression cassette comprises DNA sequences of the rice actin 1 promoter and intron (P-Os.Act1 and I-Os.Act1, U.S. Pat. No. 5,641,876, herein incorporated by reference in its entirety), operably connected to a DNA sequence encoding an *Arabidopsis thaliana* EPSPS chloroplast transit peptide (TS-At.EPSPS: CTP2, Klee et al., Mol. Gen. Genet. 210:47–442, 1987, herein incorporated by reference in its entirety), operably connected to a DNA sequence encoding a glyphosate resistant 5-enol-pyruvylshikimate-3-phosphate synthase (EPSPS) isolated from *Agrobacterium tumefaciens* sp. strain CP4 (AGRTU.aroA gene, U.S. Pat. No. 5,633,435, herein incorporated by reference in its entirety), operably connected to a DNA sequence of a nopaline synthase transcriptional terminator (T-AGRTU.nos, Fraley et al., Proc. Natl. Acad. Sci. USA 80:4803–4807,1983, herein incorporated by reference in its entirety). The second transgene expression cassette comprises a DNA sequence of a cauliflower mosaic virus 35S promoter containing a tandem duplication of the enhancer region (P-CaMV.35S:en, Kay et al., Science 236: 1299–1302, 1987; U.S. Pat. No. 5,164,316, herein incorporated by reference in its entirety), operably connected to a DNA sequence of a *Zea mays* Hsp70 intron (I-Zm.Hsp70, U.S. Pat. No. 5,424,412, herein incorporated by reference in its entirety), operably connected to a DNA sequence encoding an *Arabidopsis thaliana* EPSPS chloroplast transit peptide sequence (TS-At.EPSPS, Klee et al., Mol. Gen. Genet. 210:47–442, 1987), operably connected to a DNA sequence encoding a glyphosate resistant 5-enol-pyruvylshikimate-3-phosphate synthase (EPSPS) isolated from *Agrobacterium tumefaciens* sp. strain CP4 (AGRTU.aroA:CP4 gene, U.S. Pat. No. 5,633,435), operably connected to a DNA sequence of a nopaline synthase transcriptional terminator (T-AGRTU.nos, Fraley et al., Proc. Natl. Acad. Sci. USA 80:4803–4807, 1983).

pMON30167 (FIG. 1) is a single expression cassette identical to the first transgene expression cassette of pMON30139 as described above. pMON42411 (FIG. 2) is a single expression cassette identical to the second expression cassette of pMON30139 as described above.

After incubation of wheat cells with the *Agrobacterium* cells containing pMON42411, pMON30167 and pMON30139 constructs, glyphosate-tolerant transgenic wheat calli were selected on media containing 2 mM glyphosate for 1 week followed by transfer to a differentiation media with 0.1 mM glyphosate for 2 weeks and finally transfer to regeneration media with 0.02 mM glyphosate +0.1 µM aromatic amino acids.

Two hundred eight-four wheat events were produced from transformation with pMON42411, pMON30167 and pMON30139. These plants from pMON30139 and pMON30167 were sprayed once with 64 ounces/acre rate of glyphosate herbicide (Roundup Ultra™)/acre) to select lines for vegetative and reproductive tolerance to glyphosate herbicide (Table 1). Plants from pMON42411 were sprayed twice with 64 ounces/acre rate of glyphosate herbicide. Selection of transformed wheat plants with the single expression cassettes of pMON42411 and pMON30167 resulted in a low percentage (1.4% and 3.2%, respectively)

of wheat plants with both vegetative and reproductive tolerance. Only 3/134 plants from these constructs had acceptable levels of glyphosate herbicide tolerance. In contrast, transformed wheat plants containing the double expression cassette of pMON30139 produced a high percentage (16%) of plants with both vegetative and reproductive tolerance (24/150).

Wheat event 33391(hence forth referred to as wheat plant 33391 or wheat 33391 and includes all plant parts and seed of this plant) was selected from the 150 transgenic wheat events produced from transformation with pMON30139. Twenty-four events were selected from this population that demonstrated improved vegetative and reproductive glyphosate tolerance. Further evaluation of these 24 events was conducted for agronomic performance and the presence of a single intact insertion. Wheat 33391 was selected from this population of events. The greenhouse and field evaluations of wheat 33391 and progeny derived from wheat 33391 indicated that this transgenic insertion confers glyphosate tolerance that exceeds commercial specifications of full vegetative and reproductive tolerance to 340 g glyphosate/acre (840 g glyphosate/hectare; 32 oz of Roundup Ultra/acre) with two-fold safety margin when applied at the 3–5 leaf stage.

TABLE 1

Comparison of efficacy of single and double expression cassettes for conferring glyphosate tolerance in wheat.

| pMON# | # events tested | # events with vegetative tolerance | # veg. tolerant events with reproductive tolerance |
|---|---|---|---|
| 42411 | 71 | 26 | 1 (1.4%) |
| 30167 | 63 | 4 | 2 (3.5%) |
| 30139 | 150 | 104 | 24 (16%) |

EXAMPLE 2

Isolation of the corresponding wheat genomic flanking sequence is possible by a variety of methods known to those skilled in the art (for example, using the ligated adapters and nested PCR as described in the Genome Walker™ kit, (CloneTech Laboratories, Inc, Palo Alto, Calif.). Genomic DNA from the wheat 33391 was isolated by CTAB purification method (Rogers et al., Plant Mol Biol 5:69–76, 1985). Reagents are available commercially (see, for example Sigma Chemical Co., St. Louis, Mo.). The genomic DNA libraries for amplification were prepared according to manufacturer instructions (Genome Walker™, CloneTech Laboratories, Inc, Palo Alto, Calif.). In separate reactions, genomic DNA was subjected to restriction enzyme digestion overnight at 37° C. with the following blunt-end endonucleases: DraI, EcoRV, PvuII, ScaI, and StuI (CloneTech Laboratories, Inc. Palo Alto, Calif.). The reaction mixtures were extracted with phenol:chloroform, the DNA was precipitated by the addition of ethanol to the aqueous phase, pelleted by centrifugation, then resuspended in Tris-EDTA buffer (10 mM Tris-.HCl, pH 8.0, 1 mM EDTA). The purified blunt-ended genomic DNA fragments were then ligated to the Genome Walker™ adapters according to the manufacturer's protocol. After ligation of the adapters to the genomic DNA fragments, each reaction was heat treated (70° C. for 5 minutes) to terminate the reaction and then diluted 10-fold in Tris-EDTA buffer. One µl of each respective ligation was then amplified in a 50 µl reaction according to manufacturer's recommended protocol using an adapter-specific oligonucleotide (supplied by manufacturer) and a wheat 33391 transgene-specific oligonucleotide, such as SEQ ID NO: 1, which anneals near the 5' end of the P-Os.Act1. The PCR mixture contained 1 µl of respective adapter-ligated library, 1 µl of 10 µM Genome Walker™ adapter primer AP1 supplied by manufacturer (5'GTATATCGACTCACTATAGGGC3', SEQ ID NO:11), 1 µl of 10 µM wheat 33391 transgene specific oligonucleotide (SEQ ID NO:1), 1 µl of 10 mM deoxyribonucleotides, 5 µl of 10×PCR buffer containing MgCl$_2$, 0.5 µl (2.5 units) of Taq DNA polymerase (Boehringer Mannheim Biochemicals, Indianapolis, Ind.), and H$_2$O to 50 µl. The PCR reactions were performed in a thermocycler using calculated temperature control and the following cycling conditions: 1 cycle of 94° C. for 1 minutes; 7 cycles of (94° C. for 2 seconds, 70° C. for 3 minutes); 37 cycles of (94° C. for 2 seconds, 65° C. for 3 minutes); 1 cycle of 65° C. for 10 minutes. One µl of each primary reaction was then amplified in a secondary amplification using a "nested" adapter-specific oligonucleotide (supplied by manufacturer) and a "nested" transgene-specific oligonucleotide such as SEQ ID NO:2, which anneals to P-Os.Act1 upstream of the primer used in the primary reaction. The PCR mixture for secondary PCR contained 1 µl of respective primary PCR products, 1 µl of 10 µM Genome Walker™ nested adapter primer AP2 supplied by manufacturer (5'ACTATAGGGCACGCGTGGT3', SEQ ID NO:12), 1 µl of 10 µM wheat 33391 transgene-specific nested oligonucleotide (SEQ ID NO:2), 1 µl 10 mM deoxyribonucleotides, 5 µl of 10×PCR buffer containing MgCl$_2$, 0.5 µl (2.5 units) of Taq DNA polymerase (Boehringer Mannheim Biochemicals, Indianapolis, Ind.), and H$_2$O to 50 µl. The PCR reactions were again performed in a thermocycler using calculated temperature control and the following cycling conditions: 1 cycle of 94° C. for 1 minute; 7 cycles of (94° C. for 2 seconds), 70° C. for 3 minute; 31 cycles of (94° C. for 2 seconds, 65° C. for 3 minute); 1 cycle of 65° C. for 10 minute. PCR products, representing 5' regions that span the junction between the wheat 33391 transgenic insertion and the neighboring flanking genomic sequence were then purified by agarose gel electrophoresis followed by isolation from the agarose matrix using the QIAquick Gel Extraction Kit (catalog #28704, Qiagen Inc., Valencia, Calif.) and then directly cloned into the pGEM-T Easy vector (catalog #A1360, Promega, Madison, Wis.). The identity of the cloned PCR products was confirmed by DNA sequence analysis (ABI Prism™ 377, PE Biosystems, Foster City, Calif. and DNASTAR sequence analysis software, DNASTAR Inc., Madison, Wis.).

Similarly, the wheat 33391 3' flanking genomic DNA sequence was amplified and cloned using nested gene specific primers, such as SEQ ID NO:3, and SEQ ID NO:4, that anneal to the T-nos transcriptional terminator. Two T-nos transcriptional terminators are present in the wheat 33391 transgenic/genomic insertion, one internal in the construct and one at the 3' end of the construct adjacent to wheat genomic sequence. The PCR products produced in this reaction were sequenced and the DNA sequence that spans the junction between transgene and flanking genomic was distinguished from products of the internal T-nos by comparison to the known genetic element sequences of the pMON30139 construct.

Wheat genomic sequence flanking both sides of the transgene insertion site in the wheat genomic was determined for wheat 33391 by sequencing the Genome Walker™-derived amplification products and alignment to known transgene sequence. The sequence of a 399 base pairs (bp) segment around the insertion site was determined at the 5' end of the transgene insertion site. This segment consisted of 257 (bp) of wheat genomic sequence (nucleotide bases 1–257 of SEQ ID NO:5) and 93 bp of vector backbone sequence (nucleotide bases 258–350 of SEQ ID NO:5) and 49 bp of the 5' end of the rice Act1 promoter (nucleotide bases 251–399 of SEQ ID NO:5). Similarly, DNA sequence was determined for a 431 bp segment flanking the 3' insertion junction (SEQ ID NO:6), beginning with 32 bp of the T-nos transcriptional terminator sequence (nucleotide bases 1–32 of SEQ ID NO:6), 68 bp of vector backbone sequence (nucleotide bases 33–100) and ending with 331 bp of wheat genomic sequence flanking the transgene insertion site (nucleotide bases 101–431 of SEQ ID NO:6). Identification of wheat 33391 was performed by PCR amplification of the transgene/genomic insertion region using one primer from transgene sequence and another primer from the wheat genomic flanking sequence. The 5' transgene/genomic insertion region was confirmed by PCR amplification of a DNA amplicon to be unique to wheat 33391. This identification was demonstrated by a PCR amplicon generated by primer 5 (SEQ ID NO:7) and primer 6 (SEQ ID NO:8). Additional primer sequences can be synthesized using the DNA sequence shown in SEQ ID NO:5 that will generate amplicons of DNA length different than the amplicon generated by primer 5 and primer 6, but are still diagnostic for wheat 33391 and progeny thereof. It is within the ordinary skill in the art of a plant molecular biologist to select DNA primer sequences from SEQ ID NO:5 and develop stringent conditions for the production of an amplicon. Likewise, those skilled in the art can select DNA primer sequences from SEQ ID NO:6 that will generate amplicons diagnostic for wheat 33391. It is within the scope of this invention that DNA primer sequences derived from SEQ ID NO:5 and SEQ ID NO:6 are useful for the isolation of additional genomic DNA molecules from wheat 33391 plants, seeds and plant part by the methods disclosed herein or methods known in the art of plant molecular biologist. These additional wheat genomic DNA molecules can be isolated in a method that uses any portion of sufficient length of the DNA sequence disclosed in SEQ ID NO:5 and SEQ ID NO:6 useful as a primer or probe. The additional wheat genomic DNA molecules can be used as molecular markers diagnostic for wheat 33391.

DNA sequences that span the junction region of the wheat 33391 genomic DNA and the insert DNA of pMON30139 contained within SEQ ID NO:5 and SEQ ID NO:6 can be used as probes in a hybridization reaction to identify DNA derived from wheat 33391. For example, a DNA molecule useful as a probe from SEQ ID NO:5 would comprise the nucleotide sequence occurring from position 245–270 or its complement; a DNA molecule useful as a probe from SEQ ID NO:6 would comprise the nucleotide sequence occurring from position 87–113 or its complement. Those skilled in the art can select nucleotide sequences shorter or longer in length than those afore described that span the junction region and are useful as specific DNA probes or primers for wheat 33391 under high stringency conditions.

The PCR reaction conditions (Table 2) and quality of the extracted wheat 33391 genomic DNA are confirmed by the production of an amplicon by primer 7 (SEQ ID NO:9) and primer 8 (SEQ ID NO:10) and representing an approximately 400 bp DNA fragment from the wheat acetyl CoA carboxylase gene (Acc), a single copy endogenous gene within the wheat genome. The controls for this analysis should include a positive control from wheat 33391, a negative control from a wheat plant that is not wheat 33391, and a negative control that contains no template wheat DNA as shown in Table 2. The assay for the wheat 33391 amplicon can be performed by using a Stratagene Robocycler, MJ Engine, Perkin-Elmer 9700, or Eppendorf Mastercycler Gradient thermocycler as shown in Table 3, or by methods and apparatus known to those skilled in the art.

TABLE 2

PCR procedure and reaction mixture for the confirmation of wheat 33391 5' transgene/genomic junction region.

| Step | Reagent | Amount | Comments |
|---|---|---|---|
| 1 | Nuclease-free water | add to final volume of 20 µl | — |
| 2 | 10 × reaction buffer (with MgCl$_2$) | 2.0 µl | 1 × final concentration of buffer, 1.5 mM final concentration of MgCl$_2$ |
| 3 | 10 mM solution of dATP, dCTP, dGTP, and dTTP | 0.4 µl | 200 µM final concentration of each dNTP |
| 4 | Primer 5 (SEQ ID NO: 7) (resuspended in 1 × TE buffer or nuclease-free water to a concentration of 10 µM) | 0.4 µl | 0.2 µM final concentration |
| 5 | Primer 6 (SEQ ID NO: 8) (resuspended in 1 × TE buffer or nuclease-free water to a concentration of 10 µM) | 0.4 µl | 0.2 µM final concentration |
| 6 | Primer 7 (SEQ ID NO: 9) (resuspended in 1 × TE buffer or nuclease-free water to a concentration of 10 µM) | 0.2 µl | 0.1 µM final concentration |
| 7 | Primer 8 (SEQ ID NO: 10) (resuspended in 1 × TE buffer or nuclease-free water to a concentration of 10 µM) | 0.2 µl | 0.1 µM final concentration |
| 8 | RNase, DNase free (500 ng/µl) | 0.1 µl | 50 ng/reaction |
| 9 | REDTaq DNA polymerase (1 unit/µl) | 1.0 µl (recommended to switch pipets prior to next step) | 1 unit/reaction |

TABLE 2-continued

PCR procedure and reaction mixture for the confirmation of wheat 33391 5' transgene/genomic junction region.

| Step | Reagent | Amount | Comments |
|---|---|---|---|
| 10 | Extracted DNA (template): Samples to be analyzed | | |
| | individual leaves | 10–200 ng of genomic DNA | |
| | pooled leaves (maximum of 50 leaves/pool) | 200 ng of genomic DNA | |
| | Negative control | 50 ng of wheat genomic DNA (not wheat 33391) | |
| | Negative control | no template DNA | |
| | Positive control | 50 ng of 33391 genomic DNA | |

TABLE 3

Suggested PCR parameters for different thermocyclers
Gently mix and, if needed (no hot top on thermocycler), add 1–2 drops of mineral oil on top of each reaction.
Proceed with the PCR in a Stratagene Robocycler, MJ Engine, Perkin-Elmer 9700, or Eppendorf Mastercycler Gradient thermocycler using the following cycling parameters.

| Cycle No. | Settings: Stratagene Robocycler |
|---|---|
| 1 | 94° C. 3 minutes |
| 38 | 94° C. 1 minute |
| | 63° C. 1 minute |
| | 72° C. 1 minute and 30 seconds |
| 1 | 72° C. 10 minutes |

| Cycle No. | Settings: MJ Engine or Perkin-Elmer 9700 |
|---|---|
| 1 | 94° C. 3 minutes |
| 38 | 94° C. 10 seconds |
| | 63° C. 30 seconds |
| | 72° C. 1 minute |
| 1 | 72° C. 10 minutes |

| Cycle No. | Settings: Eppendorf Mastercycler Gradient |
|---|---|
| 1 | 94° C. 3 minutes |
| 38 | 94° C. 15 seconds |
| | 63° C. 15 seconds |
| | 72° C. 1 minute |
| 1 | 72° C. 10 minutes |

Note:
The MJ Engine or Eppendorf Mastercycler Gradient thermocycler should be run in the calculated mode. Run the Perkin-Elmer 9700 thermocycler with the ramp speed set at maximum.

EXAMPLE 3

The expression of the glyphosate resistant EPSPS protein (CP4 EPSPS) from aroA:CP4 gene can be detected by immunological methods (Rogan et al., Food Control 10:407–414, 1999, herein incorporated by reference in its entirety) from plant tissue extracts. Immunological methods such as western blots, strip tests, and enzyme linked immunosorbent assays (ELISA) have been developed to specifically detect the protein expressed from the aroA:CP4 gene contained in plant expression vectors transformed into plants. Reagents that include the polyclonal and monoclonal antibodies specific for the CP4 EPSPS are commercially available from Strategic Diagnostics (Newark, Del.). CP4 EPSPS can be detected from protein extracts of wheat 33391 plants, plant parts and seeds by immunological methods that include ELISA.

An ELISA procedure that uses 100 ng of monoclonal anti-CP4 EPSPS antibody diluted in 100 μl of 0.05 M carbonate-bicarbonate buffer pH 9.6 is absorbed to the well of a microtiter plate overnight at 4° C. The well is washed with phosphate buffered saline 0.05% Tween-20, pH 7.4 (PBS-T). The tissue is homogenized in phosphate buffered saline with a mortar and pestle or other suitable tissue grinder. The homogenate is added to the well of the microtiter plant and incubated for about 2 hours at 37° C. The well is washed three times with PBS-T. In one method, a secondary antibody, a purified rabbit anti-CP4 EPSPS is diluted to a sufficient level to provide specific binding to the CP4-EPSPS protein and incubated at 37° C. for about 1 hour. In a second method, a secondary antibody, a goat anti-CP4 EPSPS is used. A biotin-conjugated Mab anti-rabbit IgG or anti-goat IgG (Sigma Corp, St Louis Mo.) is added to the well (1:40,000 dilution in PBS) and incubated at 37° C. for 30 minutes. The well is washed three times with PBS-T. NeutrAvidin conjugated Horse radish peroxidase is diluted 1:10,000 using StabilZyme HRP-stabilizer (Sur-Modics, Eden Prairie, Minn.) and incubated at 37° C. for 15 minutes. The well is washed three times with PBS-T. The TMB substrate (Kirkegaard and Perry, Gaithersburg, Md.) is added for 10 minutes, then reaction quenched using 3 M phosphoric acid. The well is read with a microtiter plate reader at 450 nm using a reference wavelength of 650 nm. This method is an example of an ELISA suitable for detection of CP4 EPSPS and is not intended to be the only ELISA method that can be used to detect CP4 EPSPS, those skilled in the art of ELISA will know that variations to the method can be designed to provide a detection assay specific and sufficiently sensitive to detect CP4 EPSPS in a plant tissue extract.

ELISA of field grown forage of wheat event 33391 contain a mean level of 58.2±8.4 μg/g, with a range of 45.5 to 72.4 μg/g, CP4 EPSPS protein on a fresh weight tissue (fwt) basis, while the non-transgenic control forage had no detectable level of the CP4 EPSPS protein above the ELISA method's limit of detection at 0.9 μg/g fwt. Wheat event 33391 grain tissues contain a mean level of 12.6±2.5 μg/g, with a range of 9.5 to 17.6 μg/g, CP4 EPSPS protein on a fresh weight tissue (fwt) basis, while the non-transgenic control forage had no detectable level of the CP4 EPSPS protein above the ELISA method's limit of detection at 0.1 μg/g fwt. ELISA or other immunological methods for detecting CP4 EPSPS can be used as a diagnostic test for wheat 33391, when wheat 33391 progeny are the only USDA (United States Department of Agriculture) registered glyphosate tolerant wheat that expresses the CP4 EPSPS protein.

A deposit of the Monsanto Company, wheat 33391 disclosed above and recited in the appended claims has been made under the Budapest Treaty with the American Type Culture Collection (ATCC), 10801 University Boulevard, Manassas, Va. 20110. The ATCC accession number is PTA-2347. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. An isolated or recombinant DNA molecule comprising the nucleotide sequence of SEQ ID NO: 6.

2. The isolated DNA molecule of claim 1 wherein said DNA molecule has been isolated from a fertile glyphosate tolerant wheat plant.

* * * * *

```
                        SEQUENCE LISTING

<160> NUMBER OF SEQ ID NOS: 12

<210> SEQ ID NO 1
   <211> LENGTH: 32
   <212> TYPE: DNA
   <213> ORGANISM: Oryza sativa

<400> SEQUENCE: 1
cgactcaaat acagatatgc atttccaaaa gc                              32

<210> SEQ ID NO 2
   <211> LENGTH: 30
   <212> TYPE: DNA
   <213> ORGANISM: Oryza sativa

<400> SEQUENCE: 2
gactatcccg actctcttct caagcatatg                                 30

<210> SEQ ID NO 3
   <211> LENGTH: 27
   <212> TYPE: DNA
   <213> ORGANISM: Agrobacterium tumefaciens

<400> SEQUENCE: 3
catgtaatgc atgacgttat ttatgag                                    27

<210> SEQ ID NO 4
   <211> LENGTH: 30
   <212> TYPE: DNA
   <213> ORGANISM: Agrobacterium tumefaciens

<400> SEQUENCE: 4
atcgcgcgcg gtgtcatcta tgttactaga                                 30

<210> SEQ ID NO 5
   <211> LENGTH: 399
   <212> TYPE: DNA
   <213> ORGANISM: Artificial Sequence
   <220> FEATURE:
   <221> NAME/KEY: misc_feature
   <222> LOCATION: (1)..(399)
   <223> OTHER INFORMATION: chimeric sequence of wheat genome and transgene
                           insert

<400> SEQUENCE: 5
acacacgtac ccccaaacga tcagaagagg agccaaaaac ctaattccac caccgcaagt    60
ttctgtatcc acgagatccc atcttggggc ctgttccgga gctccgccgg acgagggccg   120
tcatcacgga tggcttctgc atcatcatag cctctccgat gaagtgtgag tagtttacct   180
cagaccttcg ggtccatagt tagtagctag atggcttctt ctctctcttt gaatctcaat   240
acaaagttct cccctctct aattcggaaa tctttatttc gacgtgtcta cattcacgtc    300
```

-continued

```
caaatggggg cttagatgag aaacttcacg atcgatgcgg ccgcgttaac aagcttactc    360
gaggtcattc atatgcttga gaagagagtc gggatagtc                           399

<210> SEQ ID NO 6
<211> LENGTH: 431
<212> TYPE: DNA
<213> ORGANISM: Artificial Sequence
<220> FEATURE:
<221> NAME/KEY: misc_feature
<222> LOCATION: (1)..(431)
<223> OTHER INFORMATION: chimeric sequence of wheat genome and transgene
                        insert

<400> SEQUENCE: 6
atcgcgcgcg gtgtcatcta tgttactaga tcgggatat ccccagcttg atggggatca     60
gattgtcgtt tcccgccttc agtttaaact atcagtgttt aaataattga tagaacctca   120
aataattatg acgatgtcca ggcactgatc aatacatagg catcacgtcg aagattagta   180
gatcgaagat tagtagactg acgatgtcca ggcactgatc aatacatagg gatcggggat   240
aaccaaatta ctgttgggca attgatagaa cctcaaataa ttatgacgat gtccaggcac   300
tgatcaatac ataggcatca cgtcgaagat tagtagaccg actccttcct gcatctacta   360
ctattactcc acacatcgac agttatccag catacatcta gtgtattaag ttcatggaaa   420
aacggaaatg c                                                        431

<210> SEQ ID NO 7
<211> LENGTH: 24
<212> TYPE: DNA
<213> ORGANISM: Triticum aestivum

<400> SEQUENCE: 7
cgatcagaag aggagccaaa aacc                                           24

<210> SEQ ID NO 8
<211> LENGTH: 26
<212> TYPE: DNA
<213> ORGANISM: Oryza sativa

<400> SEQUENCE: 8
cgactcaaat acagatatgc atttcc                                         26

<210> SEQ ID NO 9
<211> LENGTH: 24
<212> TYPE: DNA
<213> ORGANISM: Triticum aestivum

<400> SEQUENCE: 9
cataatggga ggcatgcttc gctg                                           24

<210> SEQ ID NO 10
<211> LENGTH: 24
<212> TYPE: DNA
<213> ORGANISM: Triticum aestivum

<400> SEQUENCE: 10
ccggttctca ctgctatctg caac                                           24

<210> SEQ ID NO 11
<211> LENGTH: 22
<212> TYPE: DNA
<213> ORGANISM: Artificial Sequence
<220> FEATURE:
```

-continued

```
<221> NAME/KEY: misc_feature
<222> LOCATION: (1)..(22)
<223> OTHER INFORMATION: fully synthetic sequence

<400> SEQUENCE: 11
gtatatcgac tcactatagg gc                                              22

<210> SEQ ID NO 12
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: fully synthetic sequence

<400> SEQUENCE: 12
actatagggc acgcgtggt                                                  19
```